United States Patent
Wojciechowicz

(10) Patent No.: US 7,302,299 B2
(45) Date of Patent: Nov. 27, 2007

(54) ELECTRICAL CONNECTOR TO TERMINATE, INSULATE AND ENVIRONMENTALLY ISOLATE A TEMPORARY CARDIAC PACING WIRE

(76) Inventor: Michael T. Wojciechowicz, 7 Finch Ct., Princeton Junction, NJ (US) 08550

( * ) Notice: Subject to any disclaimer, the term of this patent is extended or adjusted under 35 U.S.C. 154(b) by 266 days.

(21) Appl. No.: 11/088,586

(22) Filed: Mar. 24, 2005

(65) Prior Publication Data

US 2005/0283217 A1 Dec. 22, 2005

Related U.S. Application Data

(60) Provisional application No. 60/580,271, filed on Jun. 16, 2004.

(51) Int. Cl.
*A61N 1/05* (2006.01)
(52) U.S. Cl. .............. 607/119; 607/2; 607/37
(58) Field of Classification Search .......... 607/2, 607/37, 119
See application file for complete search history.

(56) References Cited

U.S. PATENT DOCUMENTS

| | | | | |
|---|---|---|---|---|
| 4,442,840 A | 4/1984 | Wojciechowicz, Jr. | ...... | 607/132 |
| 4,693,258 A | 9/1987 | Osypka et al. | ...... | 607/116 |
| 4,806,112 A * | 2/1989 | Roberts et al. | ...... | 439/144 |
| 5,350,419 A | 9/1994 | Bendel et al. | ...... | 607/132 |
| 5,456,699 A * | 10/1995 | Armstrong | ...... | 606/108 |
| 6,021,355 A | 2/2000 | Shchervinsky | ...... | 607/132 |
| 6,254,425 B1 | 7/2001 | Shchervinsky et al. | ..... | 439/502 |
| 6,397,108 B1 | 5/2002 | Camps et al. | ...... | 607/115 |
| 6,644,998 B2 | 11/2003 | Kaufmann et al. | ......... | 439/412 |
| 2003/0040784 A1 | 2/2003 | Pasternak et al. | ........... | 607/116 |

FOREIGN PATENT DOCUMENTS

DE  3304506 A1 *  8/1984

* cited by examiner

*Primary Examiner*—Carl Layno
*Assistant Examiner*—Shevon E Johnson
(74) *Attorney, Agent, or Firm*—Synnestvedt & Lechner LLP

(57) ABSTRACT

A connector device, for a temporary cardiac pacing wire, includes a conductive adaptor and a cover section which completely electrically insulates the adaptor and environmentally isolates it. The conductive adaptor comprises a contact receiving end having an aperture therein and a plug portion for plugging into a suitable medical instrument. The cover includes two clam shell sections attached by a hinge and a plug cover connected to one of the clam shell sections. In a first mode, the electrical cover completely surrounds the conductive adaptor and is locked in place so that it is secure and the plug cover is in position over the plug to completely insulate and isolate the conductive adaptor from the outside. According to a second mode, the cap is selectively removed from the plug but the two cover sections remain in place so as to expose the plug for use for connecting to medical instruments. The invention completely electrically insulates and environmentally isolates the conductive adaptor from the exterior when used in either of the two modes described.

7 Claims, 5 Drawing Sheets

ELECTRICAL CONNECTOR TO TERMINATE, INSULATE AND ENVIRONMENTALLY ISOLATE A TEMPORARY CARDIAC PACING WIRE

CROSS REFERENCE TO RELATED APPLICATIONS

This Application claims the benefit of U.S. Provisional Patent Application Ser. No. 60/580,271 filed on Jun. 16, 2004 entitled "Electrical Connector to Terminate, Insulate and Environmentally Isolate a Temporary Cardiac Pacing Wire in Such a Way as to also Allow Direct Connection to External Pacing or Monitoring Equipment" and PCT/US04/036325 filed on 29 Oct. 2004 entitled "Electrical Connector to Terminate, Insulate and Environmentally Isolate a Temporary Cardiac Pacing Wire" both by Michael T. Wojciechowicz, the entire contents and substance of which are hereby incorporated by reference.

BACKGROUND OF THE INVENTION

1. Field of the Invention

This invention relates to an electrical connector including a conductive section and an insulative cover for connection of a temporary cardiac pacing wire to external equipment.

2. Description of Related Art

Temporary cardiac pacing wires typically have one end attached to the heart during surgery and the opposite end passes through the chest with a portion exterior to the body. To aid in passing through the chest, a temporary cardiac pacing wire has a needle on the end not attached to the heart. A straight needle, also known as a Keith needle, is typically used to penetrate the chest wall from the interior and pull a portion of the temporary pacing wire outside of the body. In order to connect the body exterior end of the temporary pacing wire to pacing and/or monitoring equipment, it is necessary to create an electrical connection on the exterior exposed portion of the temporary pacing wire. Once this step is complete, the temporary pacing wire creates a direct, electrical connection to the surface of the heart. As such, the body exterior termination of the temporary pacing wire should be fully electrically insulated for safety reasons and environmentally isolated from liquids and other contaminates that may degrade its performance both when it is connected to the external equipment and especially when it is not as it is not uncommon for the temporary pacing wire to be unconnected to the external equipment for long periods of time.

The current practice to create this body exterior temporary pacing wire termination utilizes one of two methods.

The first, and most common method, illustrated in FIGS. 1A and 1B, creates the termination by utilizing the already existing Keith needle 12 used to pass the wire 10 through the chest of the patient. The needle 12 is mechanically and electrically attached to the pacing wire 10 during manufacture. After the needle 12 has been passed through the chest, it itself forms the termination. The needle 12 can then be cut at location 16 with a pair of diagonal snips or pliers 14 leaving a stub 18 as the electrical termination, however, the entire needle 12 could also be used as a less convenient "stub". Alternatively, as shown in FIG. 1B, the needle 12 could include a weakened zone 22 that can be snapped by the hands of a user 20 to produce the stub 18.

The stub 18 is then electrically insulated and sealed from the environment using a combination of improvised materials such as adhesive tape, the finger of a surgical glove, a syringe cover, a tongue depressor, and the like. When it is time for the pacing wire 10 to be connected to the external equipment, the cumbersome insulating and sealing materials must be removed to expose the stub 18. A variety of connecting cables are then used which accept the stub 18 on one end and connect it to external equipment on the other. Unfortunately, the cables do not provide a 100% electrically insulated connection, nor do they protect the connection from the environment.

U.S. Pat. No. 4,442,840, issued to Alexander Wojciechowicz, Jr. on Apr. 17, 1984, teaches an apparatus which can accept the stub pacing wire termination and both electrically insulate and environmentally isolate the stub. However, in order to connect to the external equipment, a proprietary cable must be used. It does not offer a direct connection to the external equipment. The above apparatus taught in U.S. Pat. No. 4,442,840 also uses small removable components which are easily misplaced and once missing cause the electrical insulating and environmentally isolating properties to be eliminated.

A second method of termination is taught by U.S. Pat. No. 4,693,258. It also uses a needle to pass the temporary pacing wire 10 through the chest and exterior of the body. To form its terminal connection, the pacing wire 10 must have a portion of its insulation removed immediately adjacent to the needle 12. The needle 12 is then passed through a hole in an electrically conductive pin. The needle 12 is then cut off and an insulating sleeve is passed around the pin and bare wire. The compression of the sleeve around the pin maintains the electrical contact between the exposed conductor of the pacing wire and the pin. This method allows direct connection to the external equipment, however, it does not create an electrically insulated or environmentally isolated connection as the portion of the pin which does not plug into the external equipment is uncovered and often times the uninsulated conductor of the pacing wire is also exposed due to errors in the placement of the cut when removing the needle during assembly of the apparatus.

One of the more relevant inventions is found in U.S. Pat. No. 6,644,998, entitled "Electrical Connecting Element", issued to Kaufmann et al. Described therein is a connector for a wire lead extending from the heart muscle, out of the body, and towards an external heart pacemaker. Apparently there is no needle on the end of the wire lead which passes through the exterior of the patient's body. Accordingly, this connector engages a lead end, rather than a needle, connected to a lead end. The connector is intended to engage an insulated wire lead end which is inserted through a clamping sleeve and into engagement with a squeezing contact element held by an insulation sleeve which mates with the clamping sleeve. The mating of the clamping sleeve and the insulation sleeve forces a squeezing contact element into the insulation making electrical contact with the wire lead.

Similarly, U.S. Pat. No. 6,397,108, entitled "Safety Adaptor for Temporary Medical Leads" and issued to Camps et al describes an adaptor for attaching a temporary cardiac pacing lead or analogous lead to a pacemaker or other apparatus exterior to the patient. According to one embodiment of the invention, an elongate assembly comprises a body and a door hinge together along a side edge that cooperates to receive and contain a lead including a Keith-type needle which is broken off after the lead end is inserted in the assembly. The assembly is provided with contacts which enable the assembly, upon insertion into a receptacle exterior to the apparatus, to communicate signals between the exterior apparatus and the lead contained in the assembly.

U.S. Pat. No. 6,021,355, entitled "Surgical Electrode Having a Partially Insulated Needle", issued to Slichervinsky, discloses a device in which the insulation protected end of a temporary cardiac pacing wire exits the patient's body and is intended for connection to an external pacemaker.

U.S. Pat. No. 5,350,419, entitled "Cardiac Pacing Lead", issued to Bendel, at al describes a device which provides a direction connection between the remaining portion of a Keith-type needle and an exterior apparatus.

U.S. Pat. No. 6,254,425, entitled "Electrical Connector for Cardiac Devices", issued to Slichervinsky et al, likewise describes a temporary cardiac pacing wire, including multiple conductive sections, wherein a Keith-type needle is broken to create a segment to plug into an exterior pacemaker. A branch electrode wire is inserted into a blind hole at one end of an elongate conductive wire segment to form a connector which also plugs into the pacemaker.

Finally, note U.S. patent application Publication US 2003/0040784-A1, published on Feb. 27, 2003, and entitled "Medical Lead Adapter for Storing, Isolating, Identifying and Connecting Temporary Pacing Leads" is of general interest and teaches background that relates to the general state of the prior art.

While the prior art does appear to disclose a variety of different devices for connecting a lead to a temporary cardiac pacing device, nevertheless, there does not appear to be a truly efficient and effective connector to terminate, insulate, and environmentally isolate a temporary cardiac pacing wire to the satisfaction of the surgeons that employ them and the patients that use them.

It was in the context of the foregoing prior art that the present invention arose.

SUMMARY OF THE INVENTION

Briefly described, the invention comprises an electrical connector for terminating, insulating and environmentally isolating a temporary cardiac pacing wire. The pacing wire may either be the end of the wire itself or, perhaps, a broken off Keith-type needle. The invention includes two primary parts, namely, a conductive adaptor body and an insulated cover. The conductive adaptor body has a contact receiving section, including an aperture therein for receiving the wire or stub end of the Keith-needle, and a plug section for connection to a medical device. The insulated cover includes a first and second clam shell-like cover section connected together by a hinge for surrounding the contact receiving section of the conductive adaptor body and, further, includes a cap connected by a tether or a web to a cap. Suitable locks on the cover sections permit the adaptor body to be securely held in place with the two cover sections. When the entire conductive adaptor body is covered and the cap is in place, the conductive adaptor body is completely electrically insulated and environmentally isolated from the exterior so that no stray currents can affect the patient's heart. The cap portion, however, can be selectively removed, without removing the entire cover, so that the plug may be plugged into an electrical apparatus. The adaptor is firmly held in place in the cover so that the plug can be inserted, even upside down, without risk of separating from the cover. When the cap is removed, the device can be plugged into a medical instrument, also without fear of electrical or environmental contamination.

The above invention may be further understood by reference to the following drawings.

DETAILED DESCRIPTION OF THE PREFERRED EMBODIMENT

Figure 1A:
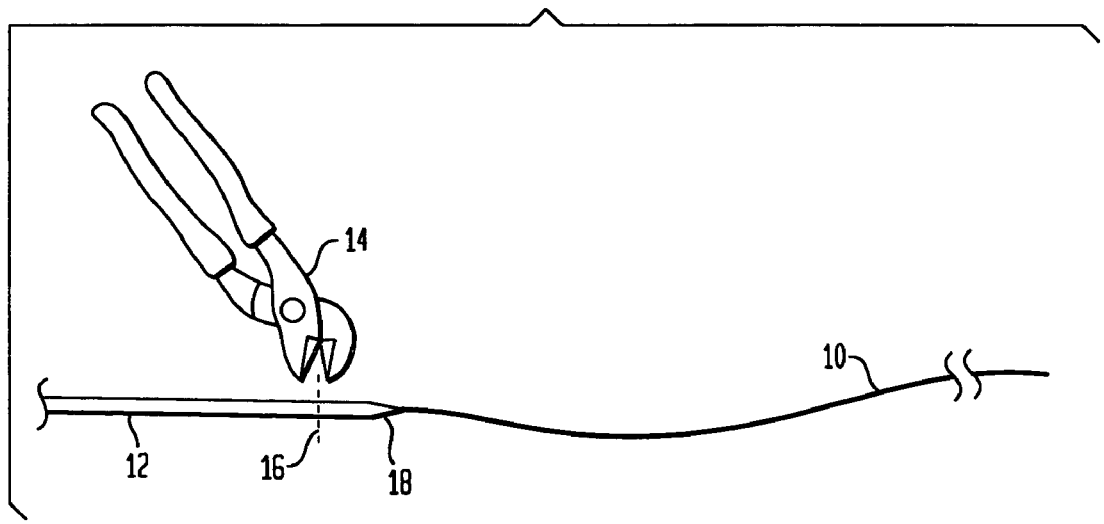
FIG. 1A illustrates the manner in which a Keith-type needle can be cut by a pair of diagonal pliers so as to produce a stub for insertion into the preferred embodiment of the invention.
Figure 1B:
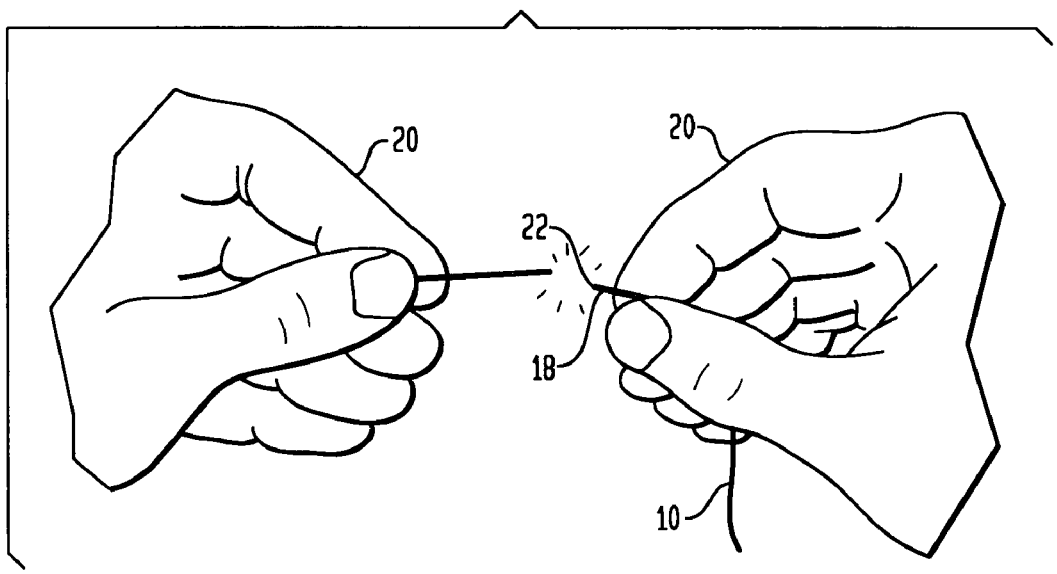
FIG. 1B illustrates an alternative procedure for producing a stub in which a Keith-type needle is broken at a weakened zone so as to produce an appropriate stub.

During the course of this description like numbers will be used to identify like elements according to the different views which illustrate the invention.

The present invention comprises an easy-to-use connector which electrically insulates and environmentally isolates the body exterior stub 18 or uninsulated wire portion 20 of a temporary cardiac pacing wire 10 and allows it to be directly connected to external equipment without the need for additional cables or interfaces. There is currently no technology which achieves these goals in a satisfactory manner.

The present invention consists of two main components, namely, an electrically conductive structure 30 and a cover 40.

Figure 2A:
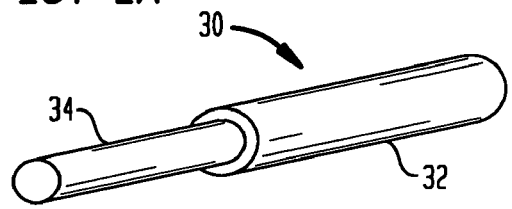
FIG. 2A is a perspective view of the conductive adaptor body.
Figure 2B:
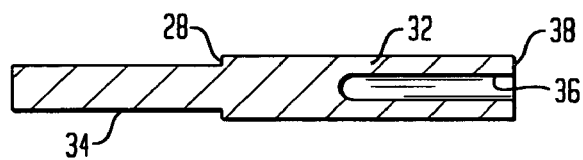
FIG. 2B is a cross-sectional view of the conductive adaptor body.
Figure 2C:
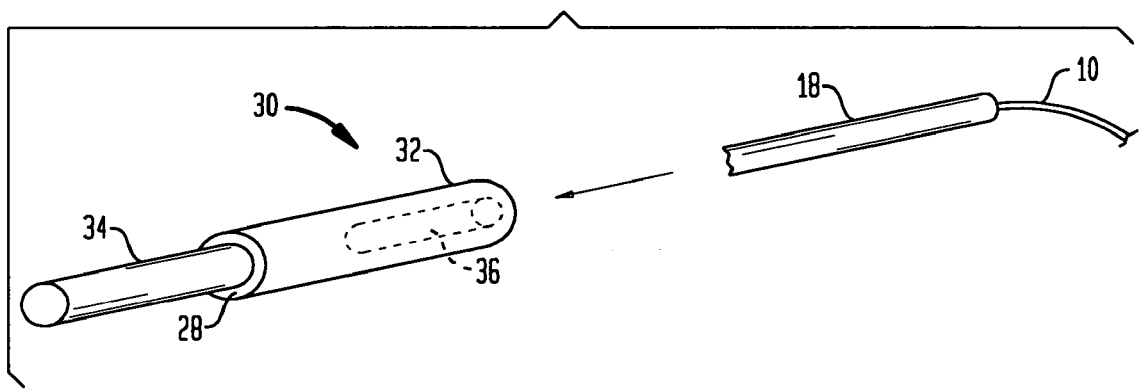
FIG. 2C illustrates the manner in which a needle, needle stub, or uninsulated wire is inserted into the aperture in the rear of the contact receiving section of the conductive adaptor body.
Figure 2D:
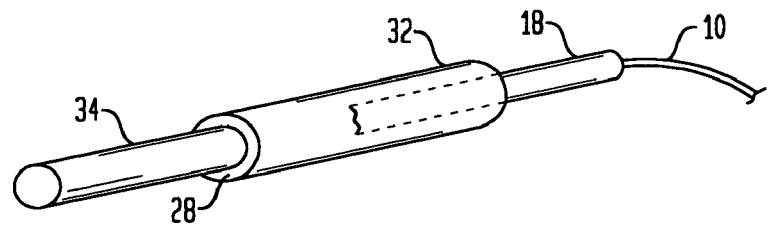
FIG. 2D illustrates the manner in which the needle, needle stub or uninsulated wire is finally receiving in the contact receiving section of the conductive adaptor body after the procedure initiated in FIG. 2C is completed.

As shown in FIGS. 2A and 2B, the electrically conductive structure of adaptor 30 includes a contact receiving end portion 32 and a plug section 34 separated by a front-facing surface 28. Adaptor 30 also includes a rear-facing surface 38 and an aperture, hole, slot, etc. 36 for accepting the stub 18, or needle 12 or bare connector 10 of the cardiac pacing wire 10. The aperture 36 can also be a groove, channel or other method for accepting a stub 18, needle 12 or wire 10. FIG. 2C illustrates the manner in which a stub 18 is inserted into the aperture 36 of the conductive adaptor 30. FIG. 2D, shows the conductive adaptor 30 after the stub 18 has been fully received in the aperture 36.

In summary, the conductive adaptor 30 comprises a male pin 34 sized to fit the female receptacle of the external equipment. The opposite end of the structure 30 includes the aperture 36, which could be a passageway, hole, tapered hole, groove, channel, or any other aperture for accepting the stub 18 or uninsulated wire portion 10 of a temporary cardiac pacing wire in such a way as to create an electrically conductive union. While the preferred embodiment of the conductive adaptor 30 is a single piece structure, it could alternatively be made by the mating of two or more conductive pieces.

The second important portion of the invention is the electrically insulated and environmentally isolated cover 40 shown in FIGS. 3A-4B. The cover 40 includes a first cover section 42 connected to a second cover section 44 by a hinge 46. First cover section 42 includes a rear portion 48 having a partial cutout section 52 therein. Similarly, the second cover section 44 includes a rear cover section 50 and a partial cutout section 54 therein.

In a similar manner, the first cover section 42 includes a front-end cover section 56 including a partial cutout portion 60 and the second cover section 44, likewise, includes a front-end section 58 including a partial cutout portion 62.

In addition to the main body of the cover 40, which comprises the first and second cover sections 42 and 44, the cover also includes a plug cap 64 connected by a tether or a portion of web 66 to either the first or second cover sections 42 or 44. Plug cap 64 includes an aperture 68 therein for receiving the plug 34. The two cover sections 42 and 44 form a hollow enclosure or aperture 70 which communicates with the contact receiving end 38 of the adaptor 30 when closed. The first cover section 42 includes three tabs 78a, 78b, and 78c which mate respectively with tab engaging latches 76a, 76b, and 76c attached to the second cover section 44 to ensure that the two cover sections 42 and 44 do not separate.

The invention essentially operates in two modes.

Figure 3A:
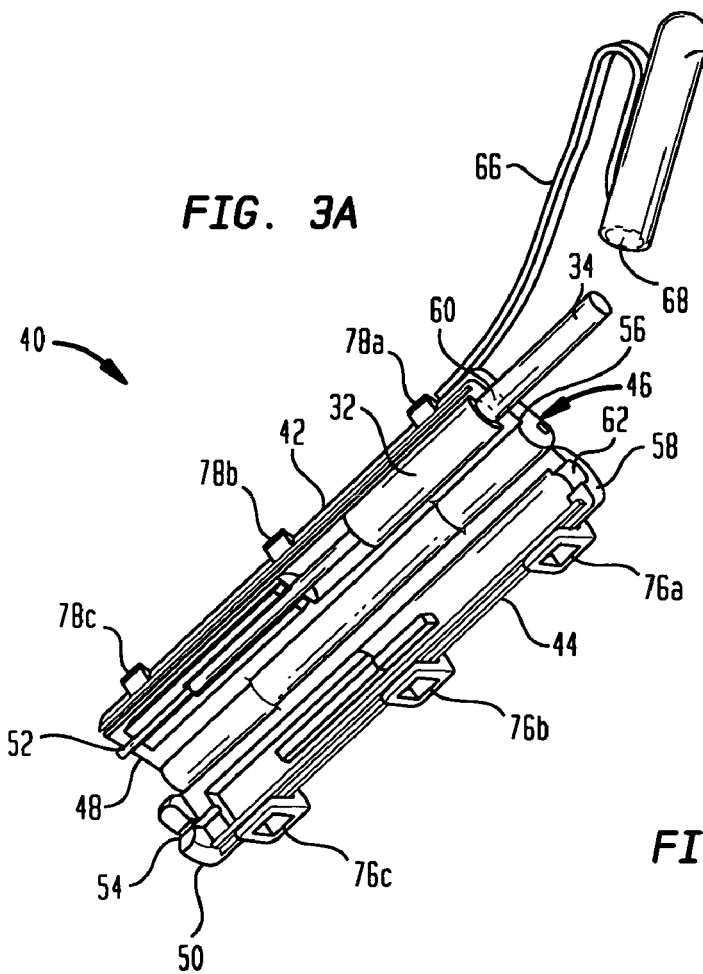
FIG. 3A illustrates the cover portion of the invention showing the first and second cover sections open.
Figure 3B:
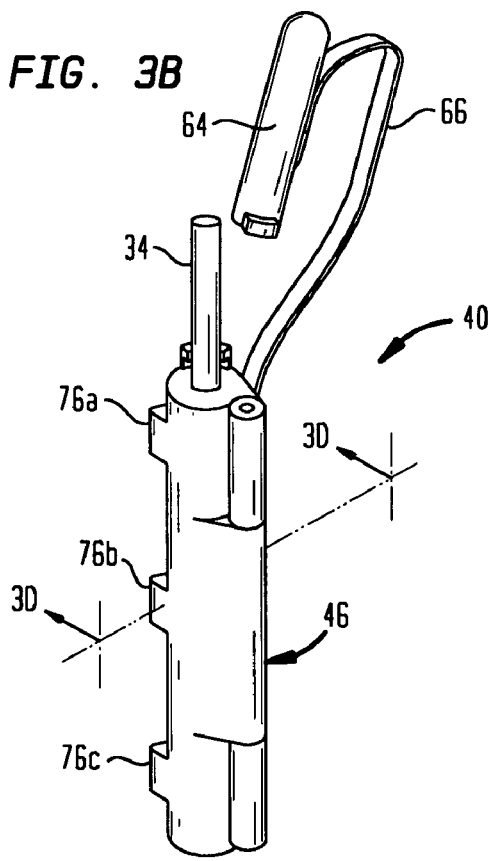
FIG. 3B illustrates the cover portion of the invention when the first and second cover section halves are closed.
Figure 3C:
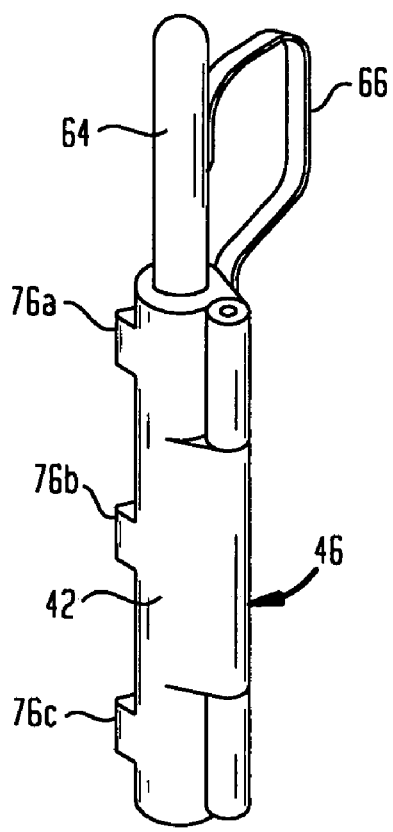
FIG. 3C is an exterior view of the cover when it completely encloses the conductive adaptor body and wherein the cap is in position on the plug end of the conductive adaptor body.
Figure 3D:
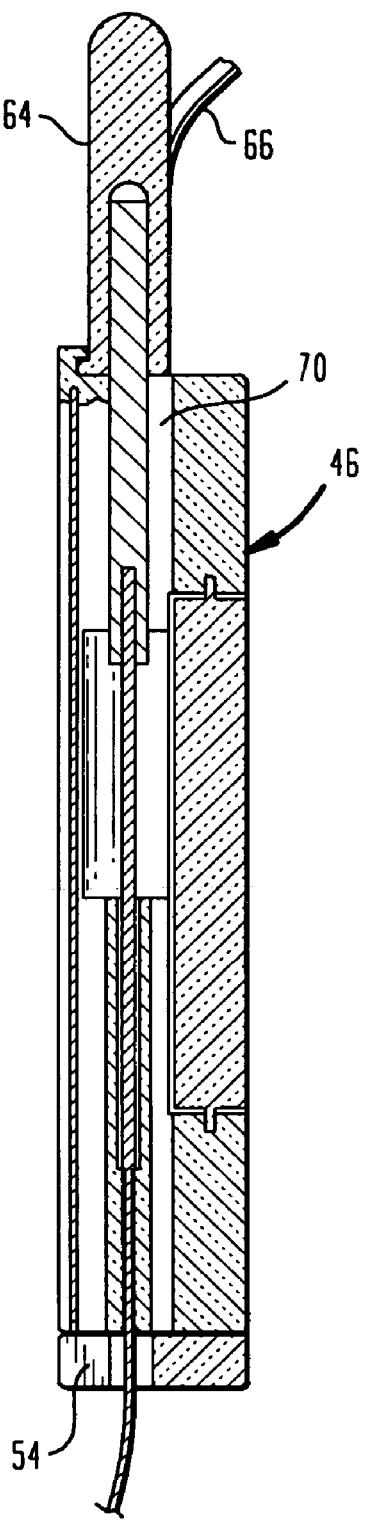
FIG. 3D is a cross-sectional view of the preferred embodiment of the invention illustrated in FIG. 3C.

According to a first mode 72, shown in FIGS. 3C and 3D, the entire conductive adaptor 30 is enclosed by the cover apparatus 40. In this mode the two cover sections 42 and 44 completely electrically insulate and environmentally isolate the contact receiving end 32 of the adaptor while the cap 64 completely covers and electrically insulates and environmentally protects the plug section 34. In this mode the entire adaptor is electrically insulated and environmentally isolated from the exterior except for the ability to receive a stub 18, Keith needle 12 or wire 10 from the temporary cardiac pacing connection.

Figure 4B:
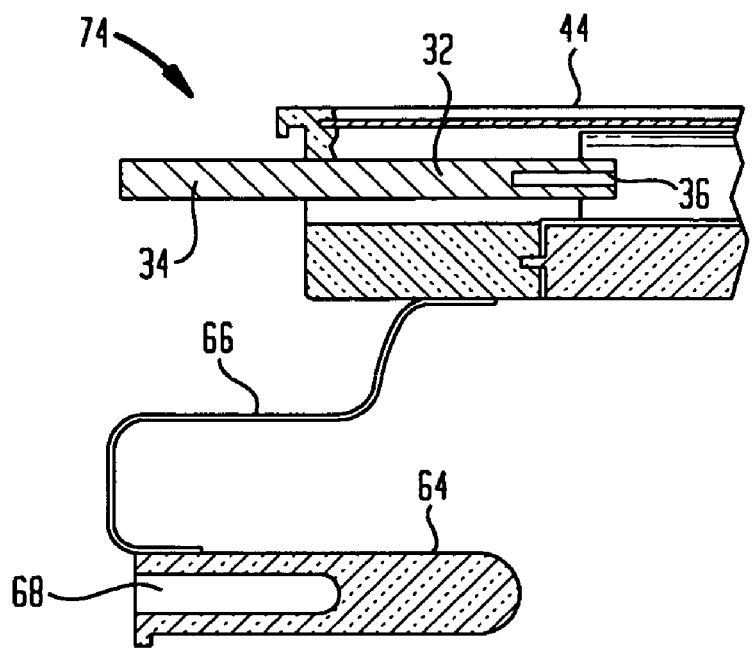
FIG. 4B is a cross-section of the preferred embodiment of the invention shown in FIG. 4A.
Figure 4A:
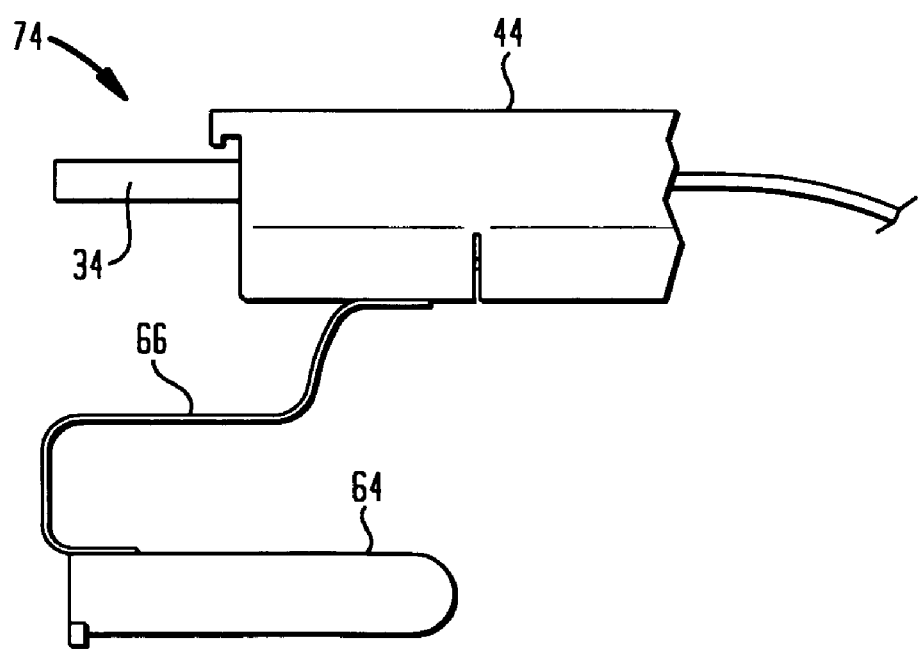
FIG. 4A illustrates the invention wherein the cover protects the contact receiving section of the adaptor body but the plug section is exposed because the cap is removed.

According to a second mode 74, illustrated in FIGS. 4A and 4B, the plug section 34 can be selectively uncapped and exposed so that it can be connected to the appropriate medical instrument.

According to the preferred embodiment of the invention, the conductive adaptor 30 is preferably metallic and formed from some suitable material such as copper, brass, etc. The cover 40 is preferably made of a suitable plastic known to those of ordinary skill in the art. While a classical hinge 46 is illustrated, a live hinge made from continuous plastic material is also a realistic alternative.

While the invention has been described with reference to the preferred embodiment, it will be appreciated by those of ordinary skill in the art that various modifications can be made to the structure and materials that comprise the invention without departing from the spirit and scope of the invention as a whole.

I claim:

1. A connector apparatus for a temporary cardiac pacing wire comprising:
    a conductive adaptor body having a contact receiving section including an aperture therein for receiving a connection from a contact attached to the heart and a plug section for connection to a medical device;
    an insulative cover means selectively attachable to said conductive adaptor body and for substantially completely electrically insulating it from electrical contact and for environmentally isolating it from environmental contact when said cover is in place and said apparatus is not connected to said medical device, wherein said insulative cover means comprises a first cover section for at least partially surrounding said contact receiving section and a second cover section for surrounding the part of the contact receiving section not covered by said first cover section, and wherein said first and second cover sections each further comprise a rear section which covers at least part of the end of said contact receiving section that receives said contact attached to said heart;
    hinge means abutting both said first and second cover sections for attaching said first and second cover sections together;
    a cap for covering said plug section of said conductive adaptor body; and,
    connector means for flexibly attaching said cap to said second cover section,
    wherein said connector means prevents said cap from being unintentionally separated from said apparatus.

2. The apparatus of claim 1 wherein said first and second rear end sections include rear cut out portions respectively so that when said cover means is in place on said contact receiving section said contact attached to said heart is effectively electrically insulated and environmentally isolate.

3. The apparatus of claim 2 wherein said first and second cover sections each further respectively comprise:
    a front end section which covers at least part of the front end of said contact section where said plug section and said contact receiving sections meet.

4. The apparatus of claim 3 wherein said front end sections each include a front cut out portion respectively for allowing said plug section to emerge from said cover means.

5. The apparatus of claim 4 wherein said aperture in said rear end of said contact receiving means is of sufficient size to snuggly receive the stub end of a needle connected to a cardiac pacing wire in an electrically conductive manner.

6. The apparatus of claim 5 wherein said hinge between said first and second cover sections is a living hinge or a common hinge having a hinge pin therein.

7. The apparatus of claim 6 wherein said aperture comprised a groove or a hole.

* * * * *